United States Patent [19]

Tonelli et al.

[11] Patent Number: 5,087,776
[45] Date of Patent: Feb. 11, 1992

[54] NEW PERFLUOROALKANES OBTAINED BY PHOTOCHEMICAL FLUORINATION AND USE THEREOF AS POLYMERIZATION INITIATORS

[75] Inventors: Claudio Tonelli; Vito Tortelli, both of Milan, Italy

[73] Assignee: Ausimont, S.p.A., Milan, Italy

[21] Appl. No.: 651,086

[22] Filed: Feb. 6, 1991

Related U.S. Application Data

[62] Division of Ser. No. 294,557, Dec. 6, 1988.

[30] Foreign Application Priority Data

Apr. 10, 1987 [IT] Italy ..................... 20061/87
Apr. 8, 1988 [WO] PCT Int'l Appl. ... PCT/EP88/00296

[51] Int. Cl.⁵ ..................... C07C 19/08; C07C 17/04; C08F 4/00
[52] U.S. Cl. ..................... 570/134; 204/157.95; 502/150; 570/136
[58] Field of Search ..................... 570/134

[56] References Cited

U.S. PATENT DOCUMENTS

| | | |
|---|---|---|
| 2,716,141 | 8/1955 | Miller ..................... 570/134 |
| 3,317,618 | 5/1967 | Haszeldine ..................... 570/134 |
| 3,917,724 | 11/1975 | Martin ..................... 260/653.1 R |
| 3,950,235 | 4/1976 | Benninger ..................... 204/59 F |
| 3,962,358 | 6/1976 | Von Halasz ..................... 260/653 |
| 4,110,474 | 8/1978 | Lagow et al. ..................... 570/134 |
| 4,281,119 | 7/1981 | Lagow et al. ..................... 570/134 |
| 4,684,452 | 4/1987 | Marchionni et al. ..................... 204/157.94 |
| 4,736,004 | 4/1988 | Scherer, Jr. et al. ..................... 526/206 |

FOREIGN PATENT DOCUMENTS

121898 10/1984 European Pat. Off. .
196630 10/1986 European Pat. Off. .

*Primary Examiner*—J. E. Evans
*Attorney, Agent, or Firm*—Morgan & Finnegan

[57] ABSTRACT

The present invention relates to branched perfluoroalkanes which, having bonds between a quaternary carbon atom and a tertiary carbon atom, easily undergo a homolytic scission of the C—C bond thereby releasing (non-persistent) radicals which may be used as initiators of polymerization of ethylenically unsaturated monomers.

A further object of the present invention are new perfluoroalkanes having at least 9 carbon atoms belonging to the above described group.

1 Claim, No Drawings

NEW PERFLUOROALKANES OBTAINED BY PHOTOCHEMICAL FLUORINATION AND USE THEREOF AS POLYMERIZATION INITIATORS

This is a divisional of co-pending application Ser. No. 07/294,557 filed Dec. 6, 1988.

FIELD OF THE INVENTION

The present invention relates to new radical initiators of polymerization of ethylenically unsaturated monomers.

BACKGROUND OF THE INVENTION

Recently increasing attention has focused on the search of new polymerization initiators, in particular of fluorinated olefins. Among such initiators the perfluoroalkyl radicals proved to be particularly interesting. At present, however, the generators of perfluoroalkyl radicals are often too stable, such as, for instance $CF_3I$ and azomethane hexafluoride, which need too high working temperatures in polymerization. See for instance: Rossi and Golden Int. J. Chem Kinetics 1979, page 775, Okafo and Whittle, Int. Journal of Chem. Kinetics, page 287 (1975) and W. A. Sheppard C. M. Sharts "Organic fluorine Chemistry" page 89 (1969).

It is also common knowledge that use may be made of perfluoroacylperoxides, which present some advantages in comparison with the above mentioned initiators; they are, however, expensive and cannot be prepared easily, moreover they may be hydrolyzed with ease. Their application on industrial scale proves to be limited.

Therefore in industrial processes use is made of non-fluorinated initiators, such as persulfates in the dispersion polymerization of fluorinated monomers, for instance of $C_2F_4$ or $C_2F_4/C_3F_6$. In that case, reactive terminals are introduced, which decrease polymer characteristics, and therefore expensive treatments of the polymer are required, in order to convert the terminal groups into non-reactive groups (D. I. Mc. Cane Encyclopedia of Polymer Science and Technology vol. 13 pages 623-670).

In European Patent 121,898 a perfluoroalkyl radical was synthetized and isolated, which was stable at room temperature and was proposed as a polymerization initiator.

This product, however, is obtained with low yields and because the product is a perfluoroalkyl radical, it requires some precautions as regards storage and treatment, in order to avoid its decomposition. Moreover the radical obtained according to this process, cannot easily be separated from the reaction raw product. This separation is generally necessary, owing to the presence of perfluoroolefines together with the perfluoroalkyl radical, as these perfluoroolefins may interfere with the polymerization monomers.

DESCRIPTION OF THE INVENTION

The object of the present invention is a process for the polymerization of ethylenically unsaturated monomers comprising as polymerization initiator a branched perfluoroalkane or a mixture of branched perfluoroalkanes having adjacent two quaternary carbon atoms or a quaternary carbon atom and a tertiary carbon atom, said perfluoroalkane having at least 9 carbon atoms.

Such perfluoroalkanes, being stable at room temperature, having practical and unlimited storage properties, do not require the precautions that were necessary for the polymerization initiators of the prior art, but can be introduced as such into the reaction medium and only at the polymerization temperature are they able to generate radicals. Known perfluoroalkanes belonging to this class are for example the following:

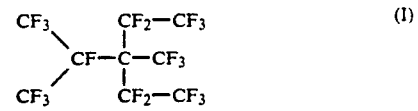

This product is prepared according to U.S. Pat. No. 3,962,358.

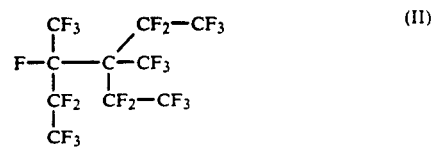

(U.S. Pat. No. 3,950,235)

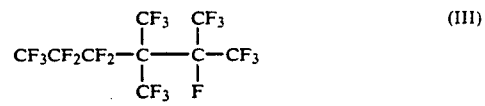

(Chemical Abstract Vol. 101, 12.153U)

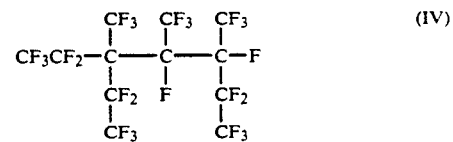

This product is prepared according to U.S. Pat. No. 3,950,235.

Other branched perfluoroalkanes belonging to this class are the new compounds having the following formulas:

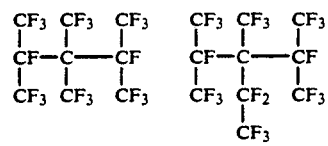

In particular compounds (V) and (VI), having adjacent two tertiary and quaternary carbon atoms, although stable at room temperature, decompose at temperatures > 70° C. preferably at temperatures > 100° C., thereby generating radicals.

For instance compounds (V) and (VI), if heated at temperatures ranging from 100° to 160° C., decompose probably undergoing a homolytic scission of the C—C bound between the tertiary and quaternary carbon atoms according to the following scheme:

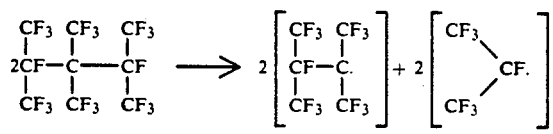

and after some time the following products are obtained, in the same ratio:

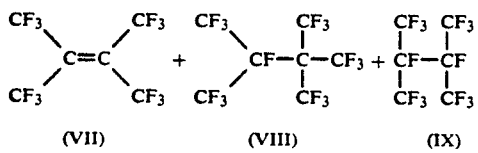

The perfluoroalkanes, having the above mentioned characteristics, are suitable for being used as polymerization initiators of halogenated or partly halogenated olefines, or mixtures thereof and of other ethylenically unsaturated monomers, and in particular of fluorinated monomers.

A further object of the present invention consists in the new branched perfluoroalkanes of formula (V) and (VI) and in their preparation by subjecting the perfluorinated olefin having the following formula:

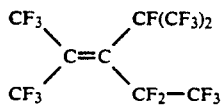

alone or in the presence of a perfluoropropene having the formula

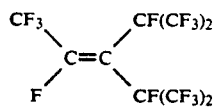

which are trimers of hexafluoropropene obtained according to U.S. Pat. No. 3,917,724 to a fluorination treatment with elemental fluorine in the presence of UV radiation at temperatures of from $-15°$ to $50°$ C., preferably of from $-10°$ to $+10°$ C.

The reaction can be carried out either in the presence of an inert gas or with fluorine alone.

The fluorination reaction according to the present invention can be suitably carried out in the liquid phase in the presence of a perfluorinated inert solvent preferably a perfluoropolyether having a molecular weight comprised within the range of from 800 to 2000 selected from the following classes:

(a) $CF_3O(C_2F_4O)_p(CF_2O)_q - CF_3$
wherein p and q are integers and the p/q ratio ranges from 1 to 0.5. The units $C_2F_4O$ and $CF_2O$ are randomly distributed along the chain;

(b) $RfO(C_3F_6O)_m(CFXO)_nRf$
wherein Rf is $CF_3, C_2F_5,$ or $C_3F_7$; X is either F or $CF_3$, m and n are integers chosen so as to fulfill the condition that the molecular weight be in the range from 800 to 2000;

(c) $C_3F_7O(C_3F_6O)_x C_2F_5$
wherein x is an integer chosen so as to fulfill the condition that the molecular weight be in the range from 800 to 2000;

(d) $R'f(CF_2CF_2O)_nR'f$
wherein n is an integer chosen so as to fulfill the above-mentioned condition and R'f is $CF_3$ or $C_2F_5$;

(e) $A(CF_2CF_2CF_2O)_nB$
wherein n is an integer chosen so as to fulfill the above condition, A is F or OR'f, and B is R'f or $C_3F_7$;

(f) perfluoropolyethers containing repeating units $(C_2F_4O), (C_3F_6O), (CFXO)$ and having a molecular weight of from 800 to 2000;

g) 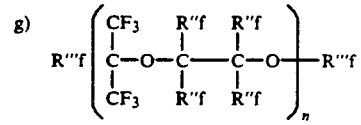

wherein R"f is a perfluoroalkyl group or F, n is an integer chosen so as to fulfil the above condition and R'''f is a perfluoroalkyl group.

The new branched perfluoroalkanes of formula (V) and (VI) are obtained according to the present invention in the presence of a new thermally stable perfluorooctane, perfluoro-2,3,4-trimethylpentane, which is described in IT-A-20060/87. This perfluorooctane can be easily removed from the perfluoroalkanes according to the present invention by rectification, since it has a lower boiling point than the branched perfluoroalkanes of the present invention.

The perfluoroalkanes of formula (V) and (VI) are obtained with a high purity degree.

EXAMPLES

The invention will now be illustrated by non-limiting examples.

EXAMPLE 1

362.2 g (0.81 moles) of trimer having formula (VII) were loaded into a 250 ml quartz reactor, having an optical path of 6.45 mm; after keeping the apparatus under $N_2$ the compound was irradiated by means of a Hg high pressure lamp (Hanau ®TQ 150, whose wavelength ranged from 250 to 400 nanometers), by maintaining a fluorine flow of 1 l/h, diluted with an equal flow of $N_2$. The reactor temperature was kept at $28°$ C. over 30 hours, the reaction course was followed by gas chromatographic analysis. At the end 358 g of raw product were unloaded and 18 g of low boiling products were collected in the traps, cooled at $-80°$ C., placed under the reactor.

The two raw products, after being collected, were subjected to rectification, thereby obtaining a first fraction consisting of perfluoroalkanes having a carbon atom number lower than or equal to 8, afterwards the following compounds (XII), (V) (VI) were isolated, in a molar ratio: 1:10:1.

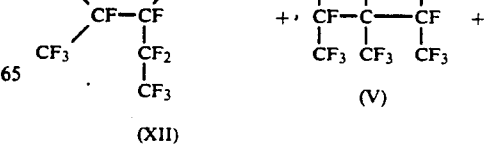

-continued $$\begin{array}{c} CF_3 \quad CF_3 \quad CF_3 \\ | \quad\quad | \quad\quad | \\ CF-C-\!\!\!-\!\!\!-CF \\ | \quad\quad | \quad\quad | \\ CF_3 \quad\quad\quad CF_3 \\ \quad\quad | \\ \quad\quad CF_2-CF_3 \end{array}$$

(VI)

Compound (XII) is a known product (S. P., Von Halasz F. Kenye and T. Martini, Chem. Ber., Vol. 106 2950-2959 (1973)).

Products (V) and (VI) were isolated in a total amount of 160 g.

The product having formula (V) had a boiling point of 140° C., whereas the product having formula (VI) had a boiling point of 153° C. at 760 mm Hg.

The structure of products (VI and (VI) was determined by gas chromatography, IR, and NMR—$^{19}$F—analysis.

The Chemical Shifts relating to NMR—$^{19}$F analysis (δ, CFCl$_3$) of product (V) were the following:

$$\begin{array}{c} (b)CF_3 \quad CF_3(c) \quad CF_3(b) \\ | \quad\quad\quad | \quad\quad\quad | \\ (a)CF-C-\!\!\!-\!\!\!-\!\!\!-CF(a) \\ | \quad\quad\quad | \quad\quad\quad | \\ (b)CF_3 \quad CF_3(c) \quad CF_3(b) \end{array}$$

(a) :161 ppm
(b) :66 ppm
(c) :55 ppm

The Chemical Shifts relating the NMR—$^{19}$F—analysis of product (VI) were the following:

$$\begin{array}{c} (b)CF_3 \quad (c)CF_3 \quad CF_3(b) \\ | \quad\quad\quad | \quad\quad\quad | \\ (a)CF-\!\!\!-\!\!\!-C-\!\!\!-\!\!\!-CF(a) \\ | \quad\quad\quad | \quad\quad\quad | \\ (b)CF_3 \quad\quad\quad CF_3(b) \\ \quad\quad | \\ \quad\quad CF_2-CF_3 \\ \quad\quad (d) \quad (e) \end{array}$$

(a) :161 ppm
(b) :66 ppm
(c) :54 ppm
(d) :92 ppm
(e) : 75 ppm

By heating perfluoroalkane (V) at 160° C. over 20 hours in sealed glass phials, one noted its complete decomposition and formation of products (VII), (VIII) (IX) in an equal molar ratio among themselves.

Perfluoroalkane (VI) underwent similar scission as well, if it was subjected to heating.

EXAMPLE 2

Into a 200 ml quartz reactor having an optical path of 6.45 mm, 81 g (0.18 moles) of a mixture containing 94% by weight of the trimer of formula (X) and 6% by weight or of the trimer of formula (XI) and 197 g of FOMBLIN ® Y, that is a perfluoropolyether belonging to class (b) and having a molecular weight 1800 were loaded.

After keeping the reactor under inert atmosphere the reaction solution having a temperature of 28° C. was irradiated by means of the Hg high pressure lamp of example 1 contemporaneously maintianing a fluorine flow of 1 l/h. After 14 hours the solution is discharged and separated from the solvent by distillation. After rectification 76 g of products are collected which according to gas chromatographic analysis contained 50% of product of formula (V) and 4% of product of formula (VI) and 15% of perfluorooctane as disclosed in IT-A-20060 A/87.

This compound is subsequently separated by perfluorononane and perfluorodecane of formula (V) and (VI) by rectification.

EXAMPLE 3

The reaction of example 2 was carried out at 15° C. After 14 hours the reaction solution was discharged and distilled in order to separate the reaction product from the solvent. 77 g of raw products were obtained, which according to gas chromatographic analysis contained 52% of compound having formula (V) and 28% of the perfluorooctane and 3% of perfluorodecane having formula (VI). The perfluorooctane is subsequently separated from the other products by rectification.

EXAMPLE 4

The reaction of example 2 was carried out at 5° C.

After 14 hours the reaction solution was discharged and distilled in order to separate the reaction product from the solvent. 80 g of raw products were obtained, which according to gas chromatographic analysis contained 43% of perfluorononane of formula (V), 31% of perfluorooctane and 2% of perfluorodecane of formula (VI).

The perfluorooctane is subsequently removed from the other compounds by rectification.

EXAMPLE 5

Following the procedure of example 1 the perfluoroalkane of formula (V) was decomposed at different temperatures and at different times. The decomposition was followed by gas chromatographic analysis the results of which are shown in the table below.

TABLE I

| Time (h) | Temperature (°C.) | % of product decomposed |
|---|---|---|
| 24 | 110 | 0.5 |
| 24 | 120 | 2.5 |
| 16 | 130 | 3.7 |
| 5 | 140 | 6 |
| 16 | 140 | 17.7 |
| 5 | 150 | 9.3 |
| 10 | 150 | 21.8 |
| 16 | 150 | 42.7 |
| 5 | 160 | 10.7 |
| 10 | 160 | 86.6 |
| 16 | 160 | 91.5 |

EXAMPLE 6

Following the procedure of example 1, the perfluoroalkane of formula (I) was decomposed at different times and temperatures. The results are reported in the following table.

TABLE II

| Time (h) | Temperature (°C.) | % of product decomposed |
|---|---|---|
| 5 | 160 | 1 |
| 10 | 160 | 1.5 |
| 16 | 160 | 2.5 |
| 8 | 180 | 12.5 |
| 16 | 180 | 24 |

EXAMPLE 7

0.05 g of perfluoroalkane (V) were loaded into a glass reactor having a volume of 30 ml and an inner diameter of 1 cm and, after degassing 2 g of $C_2F_4$ were condensed; heated at 140° C. and a few minutes later the formation was observed of a white polymeric product, insoluble in conventional organic solvents and whose IR analysis and differential thermal analysis were concordant with the typical structure of a homopolymer of $C_2F_4$.

EXAMPLE 8

0.05 g of a mixture of perfluoroalkanes (V) and (VI) in a molar ratio 10:1, 2 g of $C_2F_4$ and 6 g of $C_3F_6$ were reacted in a reactor similar to the one of the preceding example. After heating at 160° C. over 1 hour and 20 minutes the formation of a white polymeric solid was observed, with a structure (IR analysis) showing the presence of chains ($C_2F_4$) and the presence of units

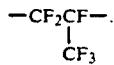

Noted was the formation of a co-polymer $C_2F_4/C_3F_6$.

EXAMPLE 9

By using the same reactor as in example 2, 0.05 g of initiator (V) and 3 g of styrene were reacted at 120° C. over 8 hours. At the end of this period of time the presence of a polymeric solid, whose analysis was concordant with the polystyrene structure, was noted in the reactor.

EXAMPLE 10

Into the same reactor as in example 7, 1.4 g of TFE (0.014 moles) and 39.04 g of perfluoroalkane of formula (V) were introduced.

The mixture was heated to 104° C. After 1 hour and 20 minutes the mixture was discharged and dried; 905 mg of a product having a molecular weight of $1.095 \times 10^6$ were obtained.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

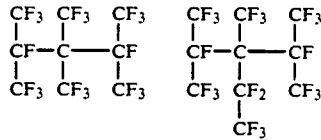

We claim:

1. Branched perfluoroalkanes having the following formulas: